United States Patent [19]

Urken

[11] Patent Number: 5,683,458
[45] Date of Patent: Nov. 4, 1997

[54] METHOD AND APPARATUS FOR AN INDWELLING ONE-WAY VALVE PROSTHESIS FOR HANDS-FREE TRACHEOESOPHAGEAL SPEECH

[75] Inventor: Mark Urken, New York, N.Y.

[73] Assignee: Mount Sinai School of Medicine of the City University of New York, New York, N.Y.

[21] Appl. No.: 664,530

[22] Filed: Jun. 17, 1996

Related U.S. Application Data

[63] Continuation-in-part of Ser. No. 450,628, May 25, 1995, abandoned.

[51] Int. Cl.$^6$ ............................................. A61F 2/20
[52] U.S. Cl. ........................................ 623/9; 623/11
[58] Field of Search ........................... 623/9, 11, 12, 623/66; 128/898

[56] References Cited

U.S. PATENT DOCUMENTS

| | | | |
|---|---|---|---|
| 4,044,402 | 8/1977 | Edwards | 623/9 |
| 4,269,184 | 5/1981 | Montgomery | 128/207.14 |
| 4,820,304 | 4/1989 | Depel et al. | 623/9 |

Primary Examiner—John G. Weiss
Assistant Examiner—Francis K. Cuddihy
Attorney, Agent, or Firm—Brumbaugh, Graves, Donohue & Raymond

[57] ABSTRACT

There is disclosed a sysem for hands-free tracheoesophageal speech in a patient who has undergone a laryngectomy, said system comprising a one-way valve prosthesis adapted to be placed in a stoma surgically created in the anterior wall of the trachea of a patient, said stoma extending through the skin of the patient thereby permitting the passage of air inwardly through the one-way valve prosthesis and into the trachea but not permitting the passage of air from the trachea outwardly through the stoma, supporting means attached to and extending laterally from the one-way valve prosthesis, said supporting means adapted to contact the anterior mucosa of the trachea around the circumference of the stoma and thereby to achieve an airtight seal between the one-way valve prosthesis and tracheal mucosa and to support the one-way valve in place in the stoma, said system thereby permitting hands-free tracheoesophageal speech by preventing exhaled air from passing outwardly through the one-way valve prosthesis and the stoma, and thus forcing said air into the pharynx through a one-way tracheopharyngeal prosthesis valve means adopted to permit the passage of air from the trachea into the pharynx but to prevent the passage of food or liquid from the pharynx into the trachea.

18 Claims, 4 Drawing Sheets

METHOD AND APPARATUS FOR AN INDWELLING ONE-WAY VALVE PROSTHESIS FOR HANDS-FREE TRACHEOESOPHAGEAL SPEECH

This is a continuation-in-part of application Ser. No. 08/450,628 filed May 25, 1995, now abandoned.

BACKGROUND OF THE INVENTION

Surgical removal of all or a portion of the larynx is an all-too-common result of various cancers of the larynx. Since laryngectomy involves the removal of the vocal cords, the loss of normal speech is unavoidable.

Following total laryngectomy there presently are three mechanisms for acquiring alaryngeal speech.

The first method is a battery powered electrolarynx that is a vibrator applied to the external skin at the cheek, submental or submandibular regions to provide a source of sound that can be subsequently modulated by the normal articulators of the oral cavity.

The second mechanism is esophageal speech which involves the swallowing of air and its subsequent regurgitation in order to produce sound.

The third mechanism, of which the present invention is an improvement, involves the use of a prosthesis with a one-way valve that is inserted into a tracheoesophageal fistula created in the posterior aspect of the tracheostome that provides a means of directing air currents generated from the lungs into the pharynx and then out through the mouth where speech is produced through the normal articulators. In order to re-direct air through this one-way valve prosthesis, the patient places a finger over the stoma during exhalation in order to achieve an occlusive seal which re-directs air posteriorly. The one-way valve within this prosthesis allows air to flow from the trachea to the pharynx but does not permit food and liquid from going in the reverse direction, from the pharynx to the trachea.

The problem with this third technique is that it requires the patient to apply his/her finger over the stoma in order to prevent the escape of air through the stoma so that it may be re-directed instead through the prosthesis.

Currently, there is a commercially available external housing device that is applied to the peristomal skin so as to cover the stoma. This device permits the patient to modulate the air pressure that closes a one-way external valve in the device thereby subsequently leading to re-direction of the remainder of the air current from the trachea into the pharynx. This housing device is applied to the entire circumference of the peristomal skin and requires a tissue adhesive in order to maintain the seal and prevent leakage of air through the prosthesis-to-skin contact. The problem with this device is that the adhesive produces a limited seal, particularly because of the architecture of the peristomal region which often has indentations as a result of prior radical neck dissection on one or both sides. It is a very rare patient who is successful in achieving hand-free speech due to this drawback of the current device, and hence the vast majority of patients are unsuccessful in using this device.

SUMMARY OF THE INVENTION

According to the invention, there is provided a prosthesis which permits hands-free tracheoesophageal speech in patients who have undergone a total or near-total laryngectomy. There is also disclosed a modified surgical procedure for the facilitated use of the prosthesis, as well as the method of using the prosthesis.

As will be described in more detail below, the prosthesis is intended to be inserted into the tracheostoma, with a one-way (i.e., inhale only) valve extending through the stoma.

In order to achieve a self-retained in-dwelling one-way valve prosthesis that permits hand-free speech, the tracheostoma is re-designed by preserving one or two tracheal rings above the point of exit of the trachea to the overlying skin. This must be done in an oncologically sound fashion so that adequate clearance between those one or two tracheal rings and the bottom of the laryngeal tumor is maintained. By preserving these rings and closing the pharynx over the top of the trachea, a closed end suprastomal tracheal pocket is created. The dimensions of the suprastomal tracheal pocket are preserved due to the underlying tracheal rings that maintain its height. By having this pocket above the stoma one can now provide an in-dwelling self-retained one-way valve prosthesis that can be inserted into the stoma. Typically this prosthesis will have flanges extending perpendicularly to the one-way valve so as to retain the prosthesis in place in the pocket. Depending upon the dimensions of the pocket, there may be a shorter cephalad flange and a longer caudal flange. This prosthesis is essentially a section through a tube that can be inserted into the tracheal lumen with the one-way valve extending through the stoma.

According to a further embodiment, the outer portion of the one way valve which extends through the stoma may be provided with a retaining ring that fits over the valve and abuts the peristomal skin. This retaining ring provides additional support to the device.

BRIEF DESCRIPTION OF THE DRAWINGS

The prosthesis according to the invention is further described below with reference to the following drawings, wherein.

DESCRIPTION OF THE PREFERRED EMBODIMENTS

Figure 1:
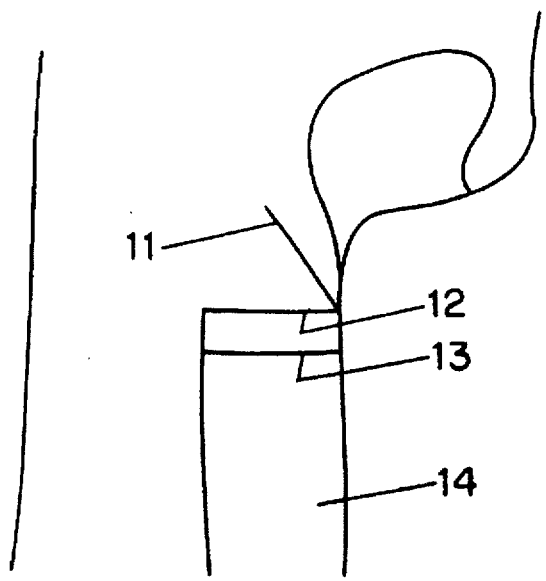
FIG. 1 is a schematic pre-operative cross-sectional sagittal view of the laryngopharynx.

Looking to FIG. 1, the pre-operative laryngopharynx is comprised of the epiglottis 11, the false vocal cord 12 and the true vocal cord 13.

Figure 2:
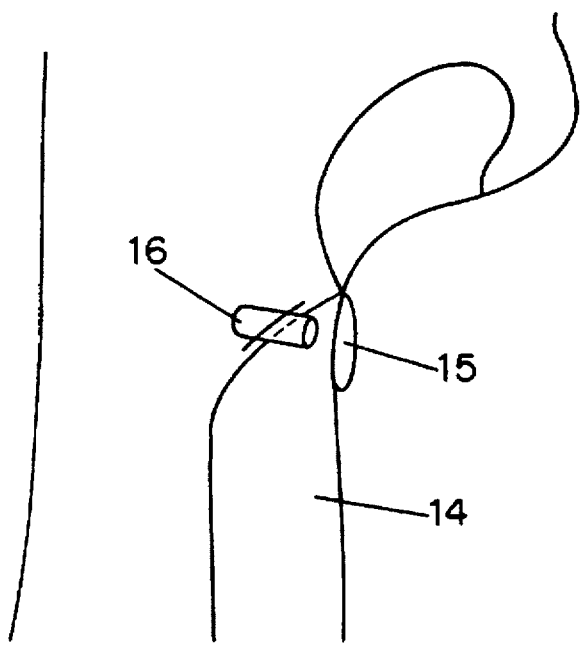
FIG. 2 is a schematic cross-sectional view of the area of FIG. 1 following conventional total laryngectomy, including a prior art tracheoesophageal prosthesis.

Comparing FIG. 1 with FIG. 2, in a conventional laryngectomy, the epiglottis, false vocal cord and true vocal cord are removed and the opening of the trachea 14 to the pharynx is surgically closed, since the epiglottis is no longer present to act as a one-way valve to prevent matter (e.g. food) other than air from passing from the pharynx into the trachea. In order to permit respiration through the trachea, a permanent stoma 15 is placed in the anterior region of the neck.

If desired, in order to permit alaryngeal speech, a tracheoesophageal prosthesis 16 may be inserted into a tracheoesophageal fistula created in the posterior wall 16 of the trachea 14. This prosthesis is a one-way valve that permits exhaled air to be passed into the pharynx and out through the mouth where speech is produced through the normal articulators. As noted previously, however, this mode of speech requires the patient to place a finger over the stoma 15 in order to create a pressure seal, thereby forcing exhaled air through the prosthesis 16.

Figure 3:
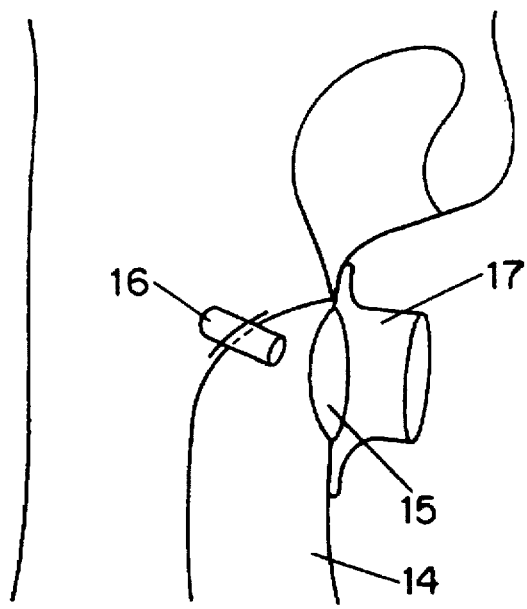
FIG. 3 is a schematic cross-sectional view as in FIG. 2, but also including an additional prior art prosthesis attached to the peristomal skin for providing hand-free speech.

As noted above, a prior attempt to eliminate the need to place a finger over the stoma involved the use of an external housing. As depicted in FIG. 3, such a housing 17 is placed over the skin surrounding the stoma 15 and held in place by a tissue adhesive. This device includes a one-way valve that permits only the passage of inhaled air, while exhaled air is forced through another one-way valve in a tracheoesophageal prosthesis 16 and thence through the mouth. When successfully attached to the skin so as to create an air-tight seal, this housing permits hands-free speech. However, only a minority of patients have remaining, post-laryngectomy, peristomal neck and skin structure that will permit an air-tight seal to be obtained. Moreover, the long-term use of an adhesive may cause irritation or even ulceration.

It is the object of the present invention to permit alaryngeal tracheoesophageal speech without the need to place a finger over the stoma, even in patients whose peristomal neck structure will not readily permit the air-tight attachment of an external one-way valve housing.

Figure 4:
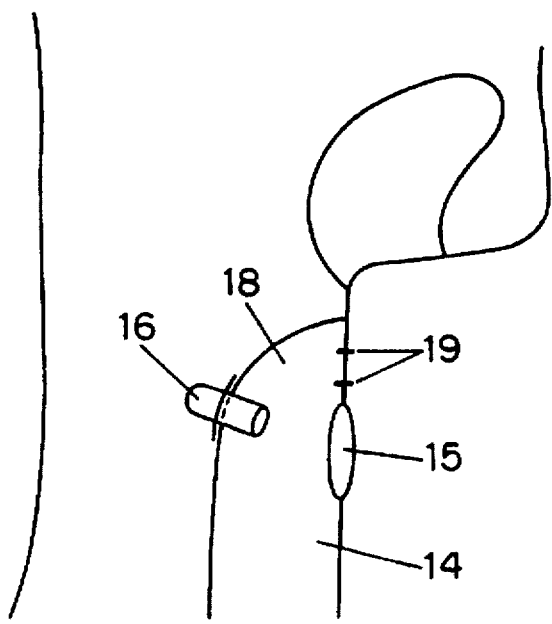
FIG. 4 is a schematic cross-sectional view of the area of FIG. 1 following modified total laryngectomy, including a suprastomal tracheal pocket for accommodating the prosthesis according to the invention.

According to the invention, and with reference to FIG. 4, a suprastomal tracheal pocket 18 is created during laryngectomy by preserving one or more tracheal rings 19 above the stoma 15. This pocket permits an in-dwelling one-way valve prosthesis to be retained in the trachea by flanges which are supported against the anterior tracheal wall, including the anterior wall of the pocket.

Figure 5:
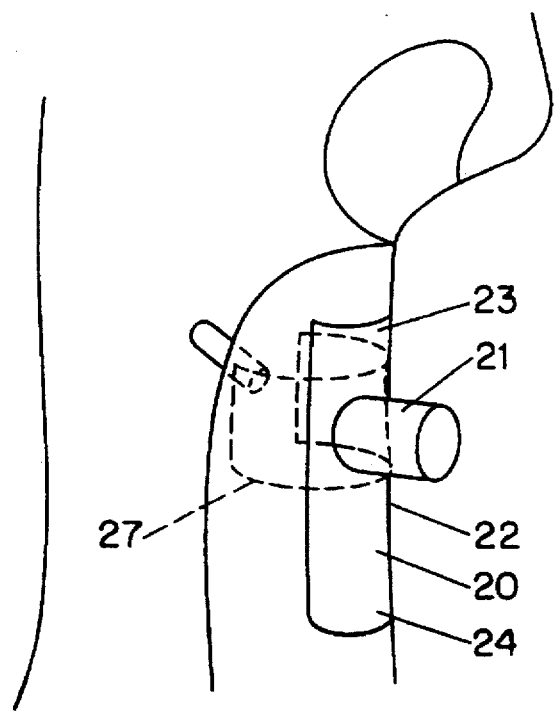
FIG. 5 is a schematic perspective view of the area of FIG. 4, including the prosthesis according to the invention.

With respect to FIG. 5, the self-retaining prosthesis 20 comprises a one-way valve 21 adapted to extend through the stoma 15. The prosthesis further comprises supporting means, preferably flanges, for supporting and retaining the prosthesis adjacent the anterior wall 22 of the trachea. This means preferably includes flange means 23, 24 extending, respectively, above and below the valve such that, when in place in the patient, the valve is retained in place in the stoma.

The one-way valve 21 is a reverse embodiment of the one-way valve of the tracheoesophageal prosthesis 16, i.e., it permits air to be inhaled into the trachea but blocks the passage of exhaled air through the valve and out through the stoma. Since the one-way valve of the prosthesis 16 does permit the passage of exhaled air out of the trachea, the two valves complement each other during respiration; the valve 21 being open during inhalation, and the valve 16 being open during exhalation and tracheoesophageal speech.

When the patient exhales and closes the one-way valve 21, this will generate pressure within the trachea behind the valve that will push the flanges 23, 24 against the anterior tracheal wall and around the circumference of the stoma, thereby to achieve an airtight seal that will then allow air to be directed posteriorly through the indwelling tracheoesophageal prosthesis and thus achieve hands-free alaryngeal speech.

One aspect of the design of the prosthesis is, therefore, the surgical creation of a new architecture for the laryngostomy. In addition, the retention of the prosthesis is not dependent upon pressure on the tracheal mucosa which would lead to erosion, ulceration and granulation of tissue. Furthermore, the retention of this device is not dependent on the external architecture of the peristomal region. It will be self-retained and the bulk of this prosthesis remains intraluminal and therefore less conspicuous than the prior external housing.

This device may be used by all total laryngectomy patients in whom the new stomal architecture, with the superstomal tracheal pocket, is created. This would be feasible in the vast majority of patients requiring total laryngectomy with the exclusion of those patients whose tumor extends to a significant extent below the level of the vocal cords thereby requiring a larger segment of trachea to be resected for oncologic clearance of the tumor.

Figure 6:
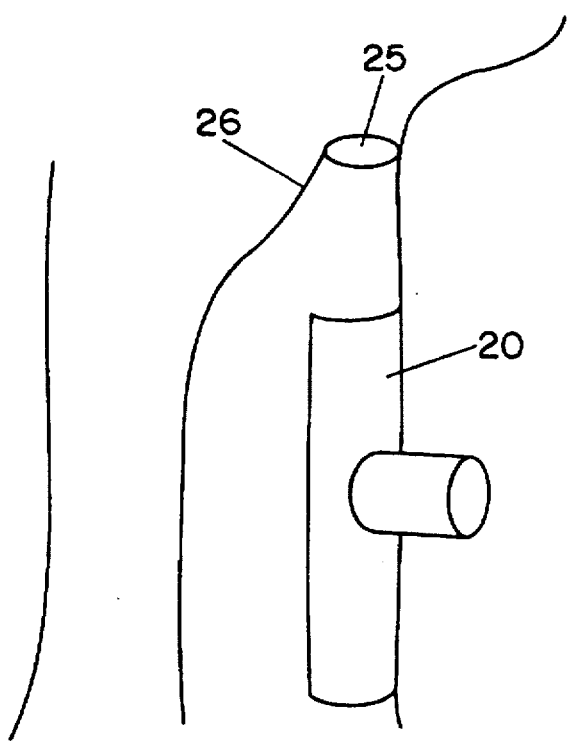
FIG. 6 is a schematic, including a tracheopharyngral shunt remaining after near-total laryngectomy, and further including the prosthesis according to the invention.

Another group of patients for whom the prosthesis according to the invention would be readily applicable are those who have undergone a near-total laryngectomy. As shown in FIG. 6, in these patients the prosthesis 20 can be inserted and hand-free speech generated through the tracheopharyngeal shunt 25 created by the normal residual mucosa of the intrinsic larynx and subglottic region. Thus in these patients, there would be no need for the tracheoesophageal prosthesis since the tracheopharyngeal shunt 25 will function as a one-way valve permitting exhaled air to pass into the mouth, while blocking food and liquid from entering the trachea. This one-way action occurs by reason of a mobile arytenoid 26 which, through sphincteric action, prevents aspiration into the trachea.

The structure of one-way valves according to the invention is known; for example the one-way valve of the prior art external housing prosthesis may be adaptable to an in-dwelling self-retained prosthesis. The supporting means may require several different sizes to accommodate variations in the dimensions of the stoma. Alternatively, a standard size may be adapted to the individual patients by trimming the flange to the appropriate dimensions.

It will also be appreciated that the supporting means may be designed with a variety of shapes and sizes, so long as they are self-supporting and self-sealing against at least the anterior wall of the trachea in the region of the stoma. A possible variation from the above-described flanges would be a full or partial ring placed in the trachea, as indicated by the broken lines 27 in FIG. 5. Depending upon the shape of the retaining means, the need for and size of the suprastomal tracheal pocket 18 may vary. As noted above, however, such a pocket is a preferred aspect of the invention in the embodiment shown where the supporting means include a cephalad flange extending upwardly from the one-way valve and adapted to press against the anterior mucosa of the pocket.

Moreover, it is contemplated according to a further embodiment that the one way valve may be provided with an outer retaining ring or the like. Such a retaining ring is shown in U.S. Pat. No. 4,269,184, but there in conjunction with a tracheal cannula unrelated to the present invention. Looking to FIG. 7, the valve 21 has flanges 23, 24 adapted, as described above, to contact the anterior mucosa of the trachea. A retaining means, preferably a retaining ring 28 may be slid over the outer end portion 29 of the valve 21. When the valve is in place within the stoma, and the flanges 23, 24 in contact with the anterior mucose, the ring may be pushed (or threaded) along this valve until it abuts the peristomal skin.

The retaining ring may be held in place by friction, for example by constructing the ring of a flexible and stretchable plastic material that frictionally engages the surface of the valve. Alternately, the valve may be provided with one or more external circumferential ridges 30, over which the ring 28 may be passed but against which the ring will be removably retained. The ridges can also be in the form of a spiral thread such that the ring may be moved along the valve by turning the ring.

Figure 7:
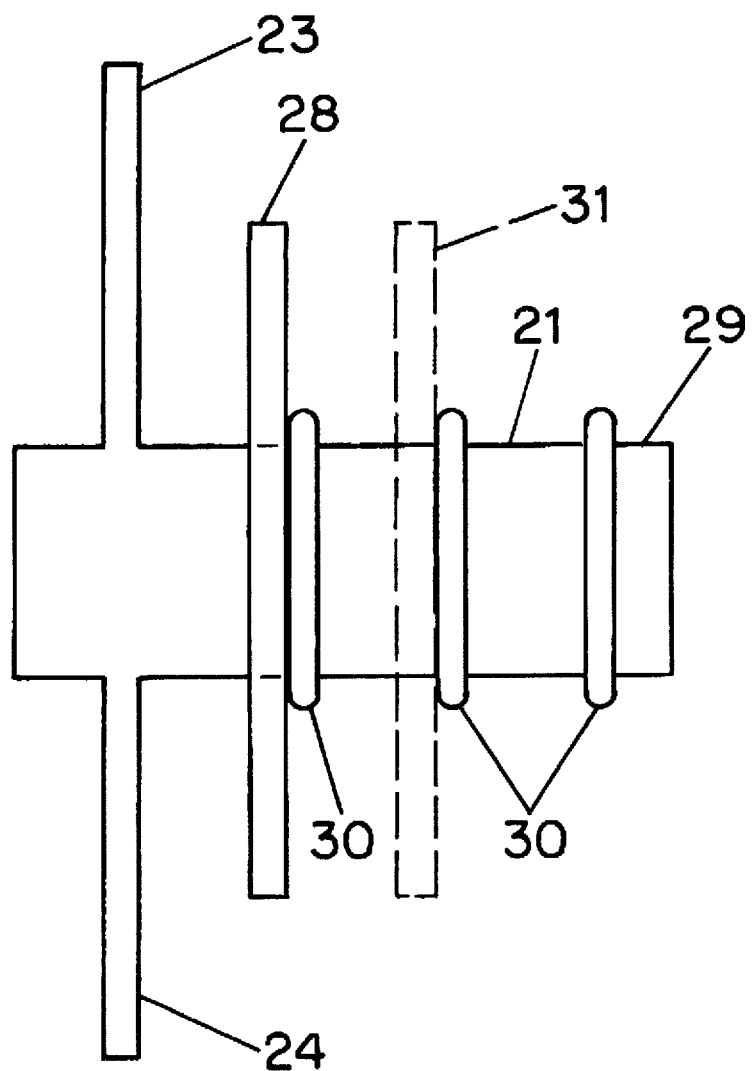
FIG. 7 is a schematic cross-sectional view of the prosthesis according to the invention, including a retaining ring on the outer portion of the valve.

By employing a plurality of ridges, or by using threads, the placement of the ring may be adjusted to accommodate various shapes or thicknesses of the anterior neck wall. As shown in FIG. 7, the ring is retained against the innermost ridge. If the neck wall of the patient were thicker, the ring could be positioned against a next outermore ridge, as shown by the broken line ring 31.

Once the ring is in place, the outer portion of the valve tube may be trimmed off. In this way, the valve may be sized to fit different patients having different neck wall thicknesses.

I claim:

1. A system for hands-free tracheoesophageal speech in a patient who has undergone a laryngectomy, said system comprising (1) a one-way valve prosthesis adapted to be placed in a stoma surgically created in the anterior wall of the trachea of a patient, said stoma extending through the skin of the patient thereby permitting the passage of air inwardly through the one-way valve prosthesis and into the trachea but not permitting the passage of air from the trachea outwardly through the stoma, supporting means attached to and extending laterally from the one-way valve, said supporting means being shaped to conform to the anterior mucosa of the trachea and thereby adapted to contact the anterior mucosa of the trachea around the circumference of the stoma and thereby to achieve an airtight seal between the one-way valve prosthesis and tracheal mucosa and to support the one-way valve prosthesis in place in the stoma, and (2) a one-way tracheoesophageal prosthesis valve means for permitting the passage of air from the trachea into the pharynx while preventing the passage of solids and liquids from the pharynx into the trachea, said system thereby permitting hands-free tracheoesophageal speech by preventing exhaled air from passing outwardly through the one-way valve prosthesis and the stoma, and thus forcing said air into the pharynx through the one-way tracheopharyngeal prosthesis valve means.

2. The system according to claim 1, wherein the supporting means include an extension adapted to contact the tracheal mucosa above said stoma and within a suprastomal tracheal pocket surgically constructed above said stoma, said pocket being created by the preservation of at least one tracheal ring above the stoma.

3. The system according to claim 2, wherein the supporting means includes a cephalad flange adapted to extend upwardly from said one-way valve and into the suprastomal tracheal pocket and to contact the anterior mucosa within said pocket, said flange being shaped essentially as a section through a tube that can be inserted into the tracheal lumen with the one-way valve extending through the stoma.

4. The system according to claim 2, wherein the one-way tracheoesophageal prosthesis valve means is a one-way valve prosthesis surgically implanted in the posterior tracheal wall.

5. The system according to claim 3, wherein the supporting means further includes a caudal flange adapted to extend downwardly from said one-way valve prosthesis and into the trachea, said caudal flange being shaped essentially as a section through a tube that can be inserted into the tracheal lumen.

6. The system according to any one of claims 1 2, 3, 4, or 5, said prosthesis further comprising retaining means adapted to slide over an outer end of the one-way valve prosthesis to be retained against the peristomal skin of the patient.

7. The system according to claim 6, wherein the retaining means comprises a ring.

8. The system according to claim 7, wherein the one-way valve prosthesis includes at least one circumferential ridge adapted to retain the ring in place against the peristomal skin.

9. The system according to claim 8, including a plurality of circumferential ridges positioned along the length of the one-way valve prosthesis, thereby permitting the ring to be retained at a plurality of positions along said valve.

10. A method of implanting a system for hands-free tracheoesophageal speech in a patient who has undergone a laryngectomy, said method comprising the steps of (1) surgically creating a stoma in the anterior wall of the trachea of the patient, said stoma extending through the skin of the patient thereby permitting the passage of air inwardly through the stoma into the trachea, (2) surgically creating a supra stomal tracheal pocket above said stoma by preserving at least one tracheal ring above the stoma, (3) implanting said system in said stoma, said system comprising a one-way valve prosthesis adapted to be placed in said stoma, and supporting means attached to and extending laterally from the one-way valve prosthesis, said supporting means adapted to contact the anterior mucosa of the trachea around the circumference of the stoma and including an extension adapted to contact and conform to the surface of the tracheal mucosa above said stoma thereby to achieve an airtight seal between the one-way valve prosthesis and tracheal mucosa and to support the one-way valve prosthesis in place in the stoma; and (4) implanting a one-way tracheoesophageal prosthesis valve means between the trachea and pharynx, said prosthesis valve adapted to permit the passage of air from the trachea into the pharynx but to prevent the passage of food or liquid from the pharynx into the trachea, said prosthesis combination thereby permitting hands-free tracheoesophageal speech by preventing exhaled air from passing outwardly through the one-way valve and the stoma, and thus forcing said air into the pharynx through the one-way tracheoesophageal prosthesis valve means.

11. The method according to claim 10, wherein said supporting means includes a cephalad flange adapted to extend upwardly from said one-way valve prosthesis and into the supra stomal tracheal pocket and to contact the anterior mucosa within said pocket, said flange being shaped essentially as a section through a tube that can be inserted into the tracheal lumen with the one-way valve extending through the stoma.

12. The method according to claim 10, wherein the one-way tracheoesophageal prosthesis valve means is a tracheoesophageal shunt surgically created from the normal residual mucosa of the intrinsic larynx and subglottic region as part of a near-total laryngectomy.

13. The method according to claim 10, wherein the supporting means further includes a caudal flange adapted to extend downwardly from said one-way valve prosthesis and into the trachea, said caudal flange being shaped essentially as a section through a tube that can be inserted into the tracheal lumen.

14. The method according to any one of claims 10, 11, 12 or 13, wherein said prosthesis further comprises retaining means adapted to slide over an outer end of the one-way valve prosthesis to be retained against the peristomal skin of the patent.

15. The method according to claim 14, wherein the retaining means comprises a ring.

16. The method according to claim 15, wherein the one-way valve prosthesis includes at least one circumferential ridge adapted to retain the ring in place against the peristomal skin.

17. The method according to claim 16, including a plurality of circumferential ridges positioned along the length of the one-way valve, thereby permitting the ring to be retained at a plurality of positions along said valve.

18. The method of implanting a system and creating a tracheopharyngeal shunt for hands-free tracheoesophageal speech in a patient who has undergone a near-total laryngectomy, said method comprising the steps of (1) surgically creating a stoma in the anterior wall of the trachea of the patient, said stoma extending through the skin of the patient thereby permitting the passage of air inwardly through the stoma into the trachea, (2) surgically creating a supra stomal tracheal pocket above said stoma by preserving at least one tracheal ring above the stoma, (3) implanting a system in said stoma, said system comprising a one-way valve prosthesis adapted to be placed in said stoma, and supporting means attached to and extending laterally from the one-way valve prosthesis, said supporting means adapted to contact the anterior mucosa of the trachea around the circumference of the stoma and further including an extension adapted to contact and conform to the surface of the tracheal mucosa above said stoma thereby to achieve an airtight seal between the one-way valve prosthesis and tracheal mucosa and to support the one-way valve prosthesis in place in the stoma; and (4) surgically creating a tracheopharyngeal shunt of the trachea above the stoma, said shunt including a mobile arytenoid that, through sphincteric action, thereby functioning as a one-way valve permitting exhaled air to pass through the shunt into the mouth while preventing solids and liquids from entering the trachea, said system and shunt thereby permitting hands-free tracheoesophageal speech.

* * * * *